United States Patent [19]

Raspanti

[11] Patent Number: 5,565,191
[45] Date of Patent: Oct. 15, 1996

[54] COSMETIC AND DERMATOLOGICAL COMPOSITIONS FOR THE PROTECTION AGAINST UV RADIATION CONTAINING STILBENE DERIVATIVES

[75] Inventor: Giuseppe Raspanti, Bergamo, Italy

[73] Assignee: 3V Inc., Weehawken, N.J.

[21] Appl. No.: 357,247

[22] Filed: Dec. 13, 1994

[30] Foreign Application Priority Data

Dec. 14, 1993 [IT] Italy ................... MI93A2613

[51] Int. Cl.⁶ .............. A61K 7/42; A61K 31/34/31/275; A61K 31/075
[52] U.S. Cl. .................. 424/59; 514/469; 514/520; 514/525; 514/533; 514/720; 549/398; 558/411; 558/416; 560/8; 568/646
[58] Field of Search .............. 424/59; 514/469, 514/520, 525, 533, 720; 549/398; 558/411, 416; 560/8; 568/646

[56] References Cited

U.S. PATENT DOCUMENTS 3,256,312  6/1966  Strobel et al. .................. 558/401

*Primary Examiner*—Shelley A. Dodson
*Attorney, Agent, or Firm*—Griffin, Butler Whisenhunt & Kurtossy

[57] ABSTRACT

Stilbene derivatives of formula (I)

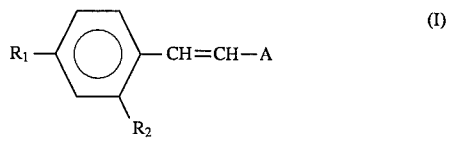

wherein A, $R_1$ and $R_2$ are as defined in the following, are useful for the protection against UV radiation.

19 Claims, No Drawings

COSMETIC AND DERMATOLOGICAL COMPOSITIONS FOR THE PROTECTION AGAINST UV RADIATION CONTAINING STILBENE DERIVATIVES

The present invention relates to cosmetic and dermatological compositions useful for the protection of the skin from UV radiation. In particular, the present invention relates to compositions containing stilbene derivatives as the active principle, a process for the preparation of said derivatives, novel stilbene derivatives having light stabilizing activity.

Ultraviolet radiation of sunlight is known to exert a damaging action on skin tissue.

In fact, prolonged exposure to sunlight is considered to be the main cause in the development of degenerative processes and of some skin tumours.

Ultraviolet radiation is also known to cause degradation of synthetic polymers.

By using particular compounds, the so-called sunscreens, which are capable of absorbing the UV part of solar radiation, the damaging effects and the ageing of the skin can be prevented or, at least, slowed down.

A number of substances have been studied and tested as protecting agents, and an extensive patent literature exists on this subject, in which compounds belonging to different chemical classes are proposed, which are capable of absorbing in the ultraviolet region, particularly the radiation from 290 to 360 nm.

Radiation from 290 to 320 nm (named UV-B) causes erythema to form, whereas the one from 320 to 400 nm (named UV-A) is responsible for skin suntan.

Sunscreens adsorbing in the UV-B region are widely used as protecting agents against sunburn; whereas the use of sunscreens to shield skin from UV-A radiations was unknown until a short time ago, except in some cases of particular therapies.

However, recent research has shown that continued and intensive UV-A radiation can also cause remarkable skin damage, particularly to persons having very sensitive, delicate skin.

Only a few of the compounds proposed up to now as sunscreens proved suitable for practical application, among these, p-methoxy-cinnamic acid and p-dimethylaminobenzoic acid esters, benzotriazoles, hydroxybenzophenones and dibenzoylmethane derivatives.

The common drawback of all these compounds is the low power thereof to absorb radiation from 290 to 360 nm, therefore it is necessary to use relatively large amounts thereof in cosmetic compositions to obtain an optimum light-protecting capability, accordingly the use thereof in practice can give rise to problems from the toxicological and economic point of view.

An optimum UV absorber should have the following characteristics:

1) high specific extinction, which means low dosages and accordingly cost-savings and a minimum toxicological risk;

2) good solubility, emulsifiability or dispersibility in the base substances commonly used for the preparation of cosmetic compositions;

3) comparatively high molecular weight, which means a lower probability of absorption by the skin tissue and a higher safety from the toxicological point of view.

It has surprisingly been found that the compounds of the present invention absorb UV radiation very effectively; therefore small amounts of these compounds are sufficient to obtain cosmetic compositions having a high SPF (sun protection factor).

The compounds of the present invention have the following general formula I

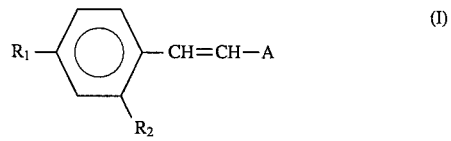

in which $R_1$ and $R_2$ are different from each other and they are hydrogen or the —CN group;

A is a group of formula II–V

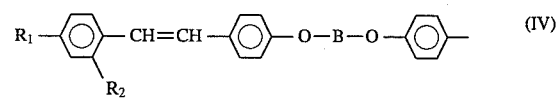

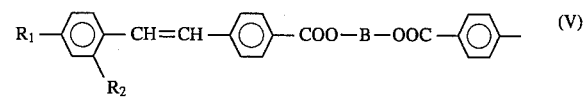

in which $R_1$ and $R_2$ have the meaning defined above, $R_3$ and $R_4$ are hydrogen, chlorine, hydroxy, $C_1$–$C_8$ straight or branched alkyl, the —$OR_9$ or —$COOR_{10}$ groups, in which $R_9$ is hydrogen or $C_1$–$C_4$ alkyl and $R_{10}$ is $C_1$–$C_{18}$ straight or branched alkyl or the group of formula VI

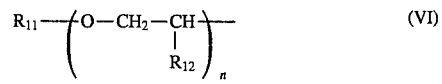

in which $R_{11}$ is $C_1$–$C_{18}$ straight or branched alkyl, $R_{12}$ is hydrogen, or methyl and n can have values from 1 to 20;

$R_5$ is hydrogen or chlorine;

$R_6$ is hydrogen or the —$OR_9$ group;

$R_7$ is hydrogen or $C_1$–$C_{18}$ straight or branched alkyl;

$R_8$ can have the meaning of $R_6$ or $R_7$;

B is a $C_2$–$C_{12}$ straight or branched alkylene residue or a divalent residue of formula VII

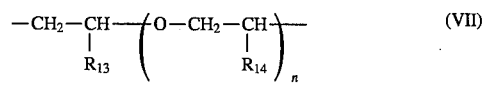

in which $R_{13}$ and $R_{14}$ can be the same or different and are hydrogen, methyl or ethyl, and n is as defined above.

General formula (I) described above, also encompasses novel compounds, in the following described by general formula Ia

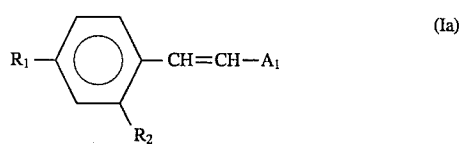

in which $R_1$ and $R_2$ have the meaning defined above and $A_1$ is a group of formula IV, V or VIII

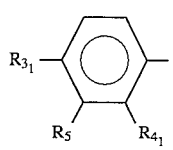

in which $R_{31}$ and $R_{41}$ can be the same or different and they are $C_1$–$C_8$ straight or branched alkyl, or the —COOR$_{10}$ group, $R_5$ and $R_{10}$ and B have the meanings defined above.

Compounds of formula I, including those of formula Ia, have a very wide absorption, which is not localized to a very restricted area of the UVA spectrum.

In fact, depending on the specific meaning of A and/or of the $R_1$–$R_{14}$ substituents, the compounds of the invention show absorption peaks in a very wide range, between 300 and 360 nm, thus being capable of exerting their light-protecting activity in both the UVA and UVB areas.

According to a preferred embodiment of the invention, the compounds of claims 5, 6, 7, 8, 9 and 10 are used as sunscreens and light-protectors.

The compounds of the invention are also valuable for use in light stabilization of synthetic polymers, in order to prevent light degradation and alteration.

The compounds of formula I show a good or sufficient solubility in the solvents or in the ingredients conventionally used for the preparation of cosmetic compositions, such as: glycerin, polyethylene glycol, lanolin, fatty acid triglycerides, polyethoxylated fatty alcohols; isopropyl myristate, palmitate, stearate; fatty alcohols, glyceryl monostearate, therefore they can also be used in the form of water-alcohol or oil-alcohol solutions thereof.

In a first embodiment of the invention, compounds of formula I can be prepared, according to procedures known to those skilled in the art, by reaction of compounds of formula IX

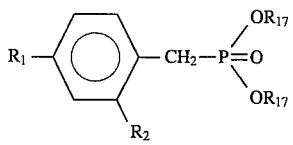

with aldehydes of formula X, XI, XII, XIII

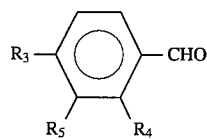

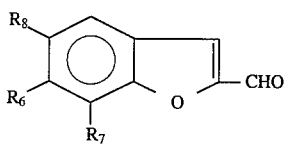

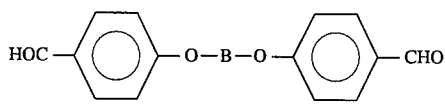

in which $R_1$–$R_8$, have the meanings defined above, $R_{17}$ is the methyl or ethyl group.

In another embodiment of the invention, compounds of formula I in which A represents groups of formula IV and V, can be prepared by alkylation of compounds of formula XIV with alkylene dihalides of formula XV or, respectively, by means of transesterification of compounds of formula XVI with divalent alcohols of formula XVII

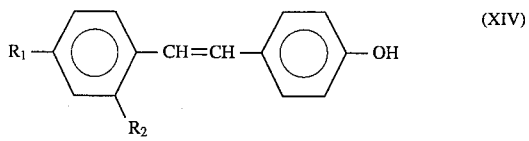

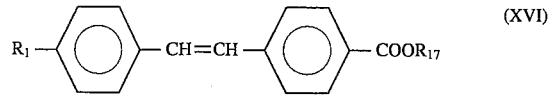

in which $R_1$, $R_2$, $R_{17}$ and B have the meanings defined above and

X is halogen, preferably chlorine or bromine.

In their turn, compounds of formula XIV and XVI are prepared by reacting phosphonate of formula IX and the corresponding aldehyde.

The compounds according to the present invention of formula XVIII

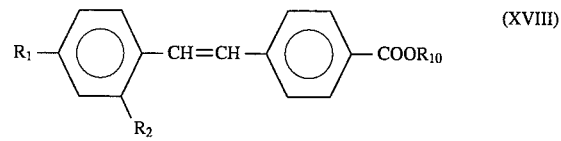

in which $R_{10}$ is alkyl with a number of carbon atoms higher than 4, are preferably prepared by transesterification of the compounds of formula XVIII in which $R_{10}$ is methyl or ethyl, with the corresponding alcohol.

From what has been stated above, the compounds of the present invention are useful as light stabilisers, in particular as light protecting agents for the skin against UVA radiation.

Therefore a further object of the invention is the use of the compounds of formula I as light stabilisers, in particular in cosmetic or dermatological compositions.

Said compositions, which are a further object of the present invention, can be prepared according to methods known to those skilled in the art.

Examples of said compositions are creams, oils, milks, ointments, emulsions, lip sticks, spray formulations, masks.

The compounds according to the present invention are added in amounts ranging from 0.1 to 20%, preferably from 1 to 15% of the weight of the cosmetic composition, depending also on the desired protection factor.

They can be added to the cosmetic formulations also in combination with other stabilisers, in order to protect the formulations themselves, for example to prevent undesired discolouration or degradation, and above all to protect the skin treated with the cosmetic formulation against the damaging action of UV-A radiation.

In the case of cosmetic compositions, they will be self-administered according to requirements of the moment. On the contrary, in the case of dermatological compositions, which can optionally contain other therapeutical agents, the dose will be determined by the physician, depending on the disease to treat and the conditions of the patient.

The following examples illustrate the present invention.

EXAMPLE 1

A mixture of 151.5 g of 2-chloromethylbenzonitrile and 200 g of triethyl phosphite is heated to 150°–160° C. and stirred for 5 hours. After that, the triethyl phosphite excess is distilled off, and subsequently benzonitril-2-diethylmethylphosphonate is also distilled under vacuum at 144°–145° C./0.8 tort.

EXAMPLE 2

Following the procedure of example 1, but using a mixture of 4-chloromethylbenzonitrile and triethyl phosphite, benzonitrile-4-diethyl-methylphosphonate is obtained.

EXAMPLE 3

27.8 g of the phosphonate of example 2 and 14 g of 4-methoxybenzaldehyde are dissolved in 80 ml of dimethylformamide. 24.3 g of a 30% KOH methanol solution are slowly added to the resulting solution. The reaction is exothermic, the temperature of the mixture is kept below 40° C. by cooling. When the KOH addition is completed, the mixture is stirred for 4 hours at 40° C. The reaction mixture, after neutralization of the residual alkalinity with acetic acid, is poured into cold water. The resulting precipitate is filtered, washed with water, dried and recrystallized with isopropanol.

21.5 g of 4-cyano-4'-methoxy-stilbene are obtained, in the form of a white substance with M.P. of 146°–148° C., and E' ($CH_3OH$): 950 at 308 nm, 1682 at 337 nm.

EXAMPLES 4–16

Following the procedure described in example 3, using the phosphonates of example 1 or 2 and aldehydes of formula X, the compounds listed in Table 1 are obtained.

TABLE 1

$R_1$—⌬—CH=CH—⌬—$R_3$ with $R_2$, $R_4$, $R_5$ substituents

| Example | $R_1$ | $R_2$ | $R_3$ | $R_4$ | $R_5$ | M.P. | E' | nm |
|---|---|---|---|---|---|---|---|---|
| 4 | H | CN | $CH_3O$— | H | H | 111–113 | 905 | 308 |
|  |  |  |  |  |  |  | 1233 | 331 |
| 5 | H | CN | H | $CH_3O$— | H | 92–94 | 719 | 294 |
|  |  |  |  |  |  |  | 918 | 333 |
| 6 | CN | H | H | $CH_3O$— | H | 84–86 | 858 | 300 |
|  |  |  |  |  |  |  | 1251 | 336 |
|  |  |  |  |  |  |  | 1271 | 312 |
| 7 | H | CN | —$COOCH_3$ | H | H | 130–132 | 1332 | 323 |
|  |  |  |  |  |  |  | 845 | 340 |
|  |  |  |  |  |  |  | 1728 | 317 |
| 8 | CN | H | —$COOCH_3$ | H | H | 156–158 | 1979 | 327 |
|  |  |  |  |  |  |  | 1323 | 343 |
| 9 | H | CN | $C_2H_5O$ | H | H | 76–78 | 807 | 308 |
|  |  |  |  |  |  |  | 1234 | 332 |
| 10 | CN | H | $CH_3$ | H | H | 184–186 | 1876 | 326 |
|  |  |  |  |  |  |  | 1175 | 307 |
| 11 | H | CN | Cl | H | H | 87–89 | 1238 | 316 |
|  |  |  |  |  |  |  | 842 | 333 |
|  |  |  |  |  |  |  | 1524 | 307 |
| 12 | CN | H | Cl | H | H | 181–183 | 1841 | 323 |
|  |  |  |  |  |  |  | 1241 | 338 |
|  |  |  |  |  |  |  | 1439 | 311 |
| 13 | CN | H | H | Cl | H | 110–112 | 1402 | 319 |
|  |  |  |  |  |  |  | 743 | 338 |
| 14 | H | CN | Cl | Cl | H | 129–131 | 948 | 309 |
|  |  |  |  |  |  |  | 883 | 322 |
|  |  |  |  |  |  |  | 1454 | 312 |
| 15 | CN | H | Cl | H | Cl | 160–162 | 1613 | 322 |
|  |  |  |  |  |  |  | 1093 | 336 |
| 16 | CN | H | H | OH | H | 177–180 | 932 | 313 |
|  |  |  |  |  |  |  | 1263 | 341 |

EXAMPLE 17

By reacting 2-formylbenzofuran with benzonitril-2-diethyl-methylphosphonate of example 1 and following the procedure of example 3, the compound of formula XIX is obtained, with M.P. of 97°–99° C. and E' 1308 at 320 nm, 1660 at 345 nm and 1291 at 261 nm.

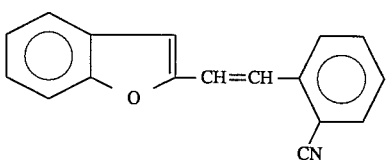

(XIX)

EXAMPLE 18

Following the procedure described in example 3, from 2-formylbenzofuran and phosphonate of example 2, the compound of formula XX is obtained, with M.P. of 157°–159° C. and E' 1611 at 336 nm, 2010 at 350 nm and 1570 at 366 nm.

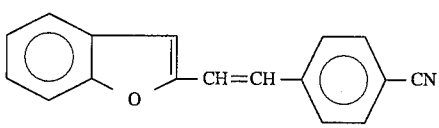
                                                                    (XX)

described in example 3, the compound of formula XXI is obtained, with M.P. 196°–199° C. and E' 862 at 308 nm, 1209 at 331 nm and 1037 at 343 nm.

EXAMPLE 19–21

0.2 ml of tetrabutylorthotitanate are added to a mixture consisting of 13.2 g of the compound of example 8 and 13 g of 2-ethylhexyl alcohol in 120 ml of xylene. The mixture is heated to 140° C., slowly distilling off xylene together with the formed methanol, for 2 hours, then it is heated to 160° C. and stirred again for 1 hour, finally applying vacuum to remove completely any xylene still present. The residue is crystallized with hexane in the presence of bleaching clay, to obtain the compound listed in Table 2.

Following the procedure described in example 19, but using other alcohols and/or the compound of example 7, the compounds listed in Table 2 are obtained.

TABLE 2

$R_1$—⟨⟩—CH=CH—⟨⟩—COOR$_{10}$
  $R_2$

| Example | $R_1$ | $R_2$ | $R_{10}$ | M.P. | E' | nm |
|---|---|---|---|---|---|---|
| 19 | CN | H | $C_4H_9$—CH($C_2H_5$)—$CH_2$— | 76–78 | 1285<br>1481<br>973 | 317<br>328<br>344 |
| 20 | H | CN | $C_4H_9$—CH($C_2H_5$)—$CH_2$— | 48–50 | 964<br>1013<br>662 | 315<br>324<br>339 |
| 21 | CN | H | $C_4H_9O$—$CH_2$—$CH_2$— | 151–154 | 1297<br>1476<br>996 | 318<br>328<br>344 |

EXAMPLE 22–24

Following the procedure described in example 19, but using divalent alcohols for transesterification, the compounds listed in Table 3 are obtained.

TABLE 3

| Example | $R_1$ | $R_2$ | B | M.P. | E' | nm |
|---|---|---|---|---|---|---|
| 22 | CN | H | $CH_2$—C($CH_3$)$_2$—$CH_2$— | 149–151 | 1690<br>1949<br>1285 | 317<br>327<br>343 |
| 23 | CN | H | —$(CH_2)_{10}$— | 213–215 | 1457<br>1659<br>1084 | 317<br>327<br>343 |
| 24 | CN | H | —$CH_2$—$CH_2(O$—$CH_2$—$CH_2)_2$ | 192–195 | 1494<br>1728<br>1134 | 317<br>327<br>343 |

EXAMPLE 25

From butylene-1,4-bis (p-oxybenzaldehyde) and the phosphonate of example 1, following the procedure

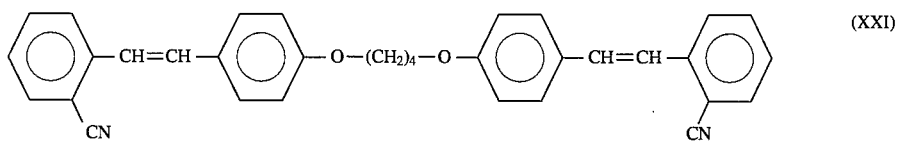

EXAMPLE 26

Preparation of a sun cream.

A mixture consisting of 10 g of cyclodimeticone/dimeticone copolymer (Dow Corning Q 2-3223), 10 g of cyclometicone (Dow Corning 344), 0.5 g of polysorbate 20 (Tween 20) and 3 g of the compound of Example 6 is prepared.

This mixture is added to a previously prepared solution of 0.2 g of 1,1'-methylene-bis-3-(3'-hydroxymethyl- 2,4-dioxyimidazolidinyl)urea, 0.05 g of methyl paraben and 76.25 g of water, stirring until obtaining a homogeneous cream.

I claim:

1. A method of protecting skin from UV radiation comprising applying to the skin an effective amount of an active ingredient selected from the compounds of formula I:

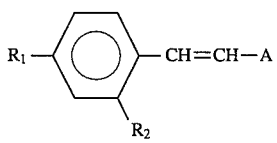

in which $R_1$ and $R_2$ are different from each other and are hydrogen or a —CN group;
A is a group of formula II–V

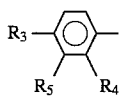

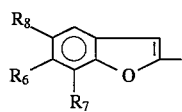

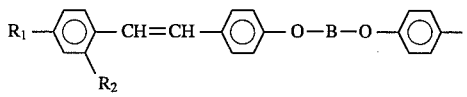

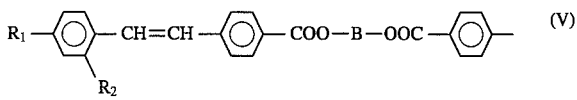

in which $R_1$ and $R_2$ have the meaning defined above, $R_3$ and $R_4$ are hydrogen, chlorine, hydroxy, $C_1$–$C_8$ straight or branched alkyl, —$OR_9$ or —$COOR_{10}$ groups, in which $R_9$ is hydrogen or $C_1$–$C_4$ alkyl and $R_{10}$ is $C_1$–$C_{18}$ straight or branched alkyl or a group of formula VI

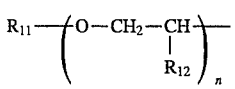

in which $R_{11}$ is $C_1$–$C_{18}$ straight or branched alkyl, $R_{12}$ is hydrogen, or methyl and n can have values from 1 to 20, $R_5$ is hydrogen or chlorine, $R_6$ is hydrogen or an —$OR_9$ group, $R_7$ is hydrogen or $C_1$–$C_{18}$ straight or branched alkyl, $R_8$ can have the meaning of $R_6$ or $R_7$, B is a $C_2$–$C_{12}$ straight or branched alkylene residue or a divalent residue of formula VII

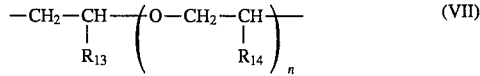

in which $R_{13}$ and $R_{14}$ can be the same or different and are hydrogen, methyl or ethyl, and n is as defined above.

2. A method according to claim 1, wherein said active ingredient is selected from the compounds of formula Ia

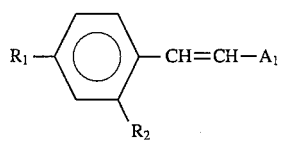

in which $R_1$ and $R_2$ have the meanings defined above and $A_1$ is a group of formula IV, V or VIII

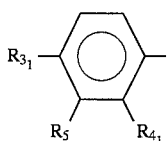

in which $R_{31}$ and $R_{41}$ can be the same or different and are $C_1$–$C_8$ straight or branched alkyl, or the —$COOR_{10}$ group, $R_5$ and $R_{10}$ and B have the meanings defined above.

3. A method according to claim 1, wherein said active ingredient is selected from the compounds of formula XXII:

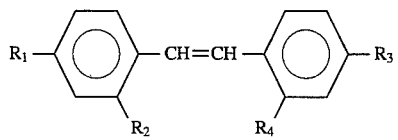

4. A method according to claim 1, wherein said active ingredient is selected from the compounds of formula XXIII

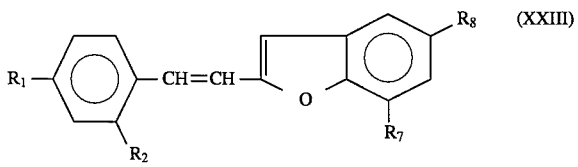

in which $R_1$, $R_2$, $R_7$ and $R_8$ have the meanings defined above.

5. A method according to claim 1 wherein said active ingredient is selected from the compounds of formula XXIV

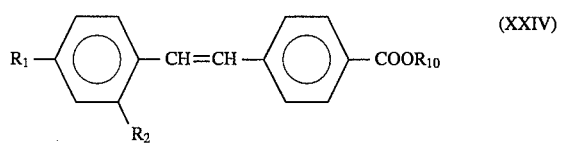

6. A method according to claim 1 wherein said active ingredient is selected from the compounds of formula XXV

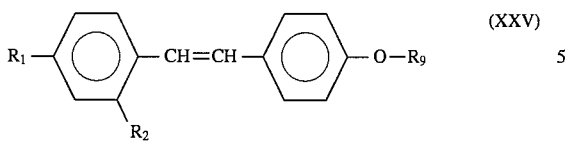
(XXV)

7. A method according to claim 1 wherein said active ingredient is selected from the compounds of formula XXVI

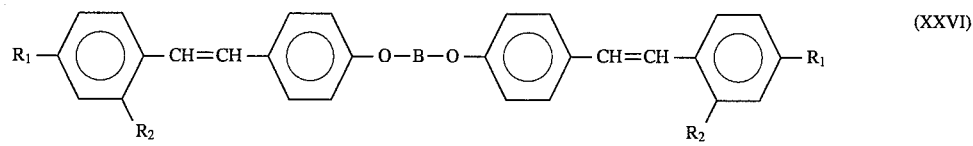
(XXVI)

8. A method according to claim 1 wherein said active ingredient is selected from the compounds of formula XXVII

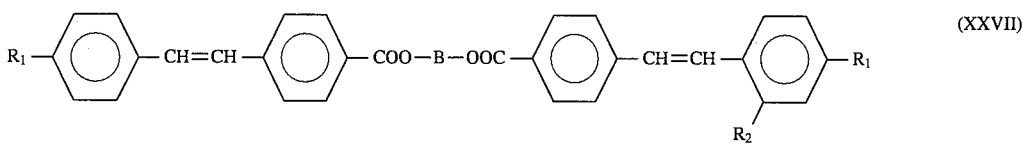
(XXVII)

9. A composition for topical application to skin comprising a suitable non-toxic base material and an active ingredient selected from the compounds of formula I:

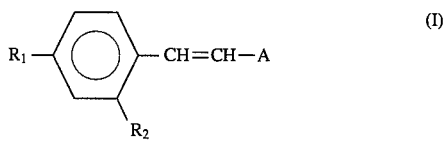
(I)

in which $R_1$ and $R_2$ are different from each other and they are hydrogen or a —CN group;
A is a group of formula II–V

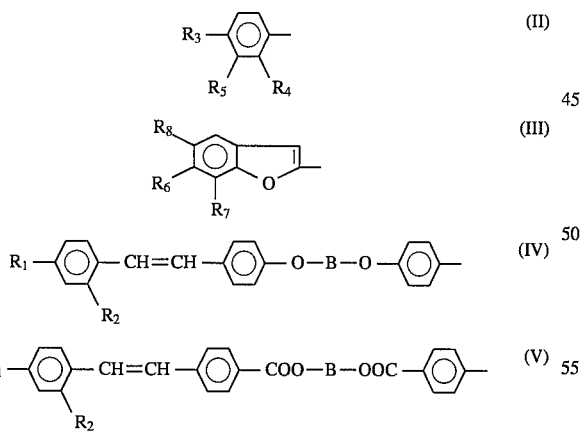
(II)
(III)
(IV)
(V)

in which $R_1$ and $R_2$ have the meaning defined above, $R_3$ and $R_4$ are hydrogen, chlorine, hydroxy, $C_1$–$C_8$ straight or branched alkyl, —$OR_9$ or —$COOR_{10}$ groups, in which $R_9$ is hydrogen or $C_1$–$C_4$ alkyl and $R_{10}$ is $C_1$–$C_{18}$ straight or branched alkyl or a group of formula VI

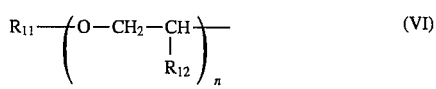
(VI)

in which R11 is $C_1$–$C_{18}$ straight or branched alkyl, $R_{12}$ is hydrogen, or methyl and n can have values from 1 to 20, $R_5$ is hydrogen or chlorine, $R_6$ is hydrogen or an —$OR_9$ group, $R_7$ is hydrogen or $C_1$–$C_{18}$ or branched alkyl, $R_8$ can have the meaning of $R_6$ or $R_7$, B is a $C_2$–$C_{12}$ straight or branched alkylene residue or a divalent residue of formula VII

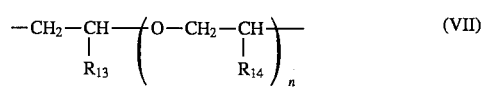
(VII)

in which $R_{13}$ and $R_{14}$ can be the same or different and are hydrogen, methyl or ethyl, and n is as defined above.

10. A composition according to claim 9, wherein said active ingredient is selected from the compounds of formula Ia

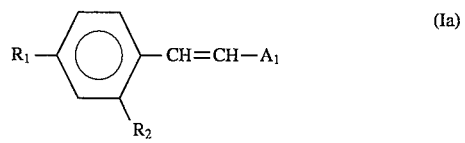
(Ia)

in which $R_1$ and $R_2$ have the meanings defined above and $A_1$ is a group of formula IV, V or VIII

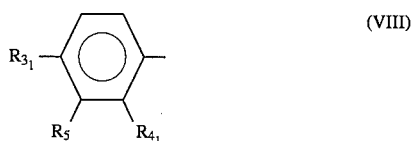
(VIII)

in which $R_{31}$ and $R_{41}$ can be the same or different and are $C_1$–$C_8$ straight or branched alkyl, or the —$COOR_{10}$ group, $R_5$ and $R_{10}$ and B have the meanings defined above.

11. A composition according to claim 9 wherein said active ingredient is selected from the compounds of formula XXII

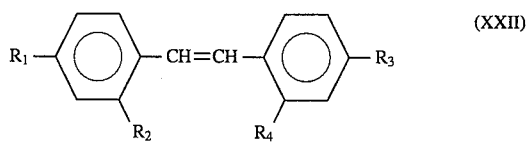
(XXII)

in which $R_1$–$R_4$ have the meanings defined above.

12. A composition according to claim 9, wherein said active ingredient is selected from the compounds of formula XXIII

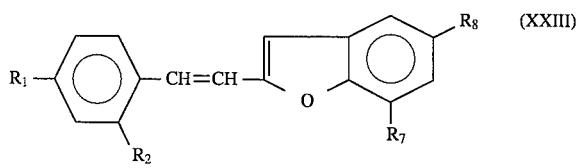 (XXIII)

in which $R_1$, $R_2$, $R_7$ and $R_8$ have the meanings defined above.

13. A composition according to claim 9 wherein said active ingredient is selected from the compounds of formula XXIV

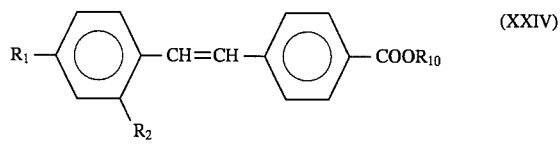 (XXIV)

14. A composition according to claim 9 wherein said active ingredient is selected from the compounds of formula XXV

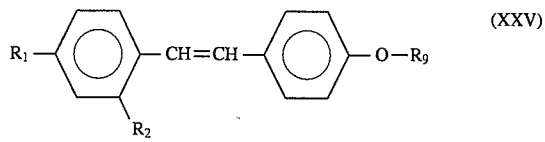 (XXV)

15. A composition according to claim 9 wherein said active ingredient is selected from the compounds of formula XXVI

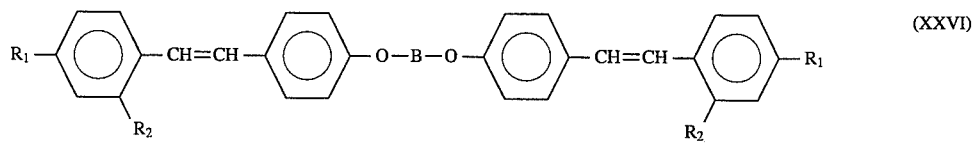 (XXVI)

16. A composition according to claim 9 wherein said active ingredient is selected from the compounds of formula XXVII

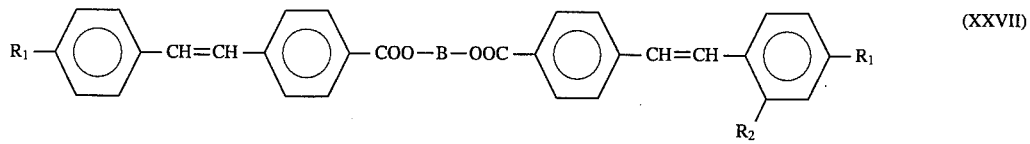 (XXVII)

17. A composition according to claim 9, containing from 0.1 to 20% by weight of compounds of formula I.

18. A composition according to claim 9, containing from 1 to 15% by weight of compounds of formula I.

19. A compound of formula Ia

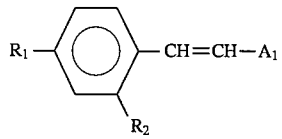 (Ia)

in which $R_1$ and $R_2$ are different from each other and are hydrogen or a —CN group, and $A_1$ is a group of formula IV, V or VIII

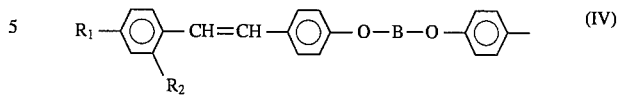 (IV)

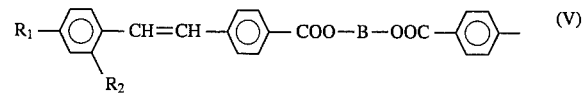 (V)

in which $R_1$ and $R_2$ have the meaning defined above, $R_3$ and $R_4$ are hydrogen, chlorine, hydroxy, $C_1$–$C_8$ straight or branched alkyl, —$OR_9$ or —$COOR_{10}$ groups, in which $R_9$ is hydrogen or $C_1$–$C_4$ alkyl and $R_{10}$ is $C_1$–$C_{18}$ straight or branched alkyl or a group of formula VI

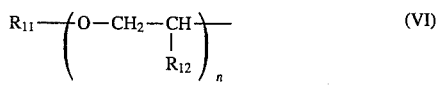 (VI)

in which $R_{11}$ is $C_1$–$C_{18}$ straight or branched alkyl, $R_{12}$ is hydrogen, or methyl and n can have values from 1 to 20, $R_5$ is hydrogen or chlorine, B is a $C_2$–$C_{12}$ straight or branched alkylene residue or a divalent residue of formula VII

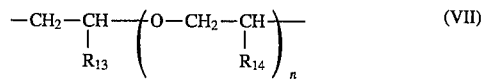 (VII)

in which $R_{13}$ and $R_{14}$ can be the same or different and are hydrogen, methyl or ethyl, and n is as defined above

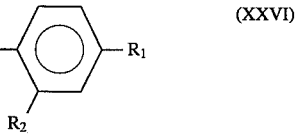 (VIII)

in which $R_{31}$ and $R_{41}$ can be the same or different and are $C_1$–$C_8$ straight or branched alkyl, or the —$COOR_{10}$ group.

\* \* \* \* \*